(12) United States Patent
Otsubo (10) Patent No.: US 7,160,408 B2
(45) Date of Patent: Jan. 9, 2007

(54) PROCESS FOR MAKING A DISPOSABLE DIAPER

(75) Inventor: Toshifumi Otsubo, Kagawa-ken (JP)

(73) Assignee: Uni-Charm Corporation, Ehime-ken (JP)

( * ) Notice: Subject to any disclaimer, the term of this patent is extended or adjusted under 35 U.S.C. 154(b) by 320 days.

(21) Appl. No.: 10/725,584

(22) Filed: Dec. 3, 2003

(65) Prior Publication Data

US 2004/0108043 A1   Jun. 10, 2004

(30) Foreign Application Priority Data

Dec. 10, 2002 (JP) ............................. 2002-358465

(51) Int. Cl.
*A61F 13/15* (2006.01)
*B32B 37/00* (2006.01)

(52) U.S. Cl. ...................... 156/163; 156/164; 156/161; 156/229; 156/227; 156/204

(58) Field of Classification Search ................ 156/161, 156/163, 164, 229, 227, 204
See application file for complete search history.

(56) References Cited

U.S. PATENT DOCUMENTS

| 5,711,832 | A | * | 1/1998 | Glaug et al. ................ 156/73.1 |
| 5,870,778 | A | * | 2/1999 | Tharpe ........................... 2/400 |

FOREIGN PATENT DOCUMENTS

| JP | 6-54878 | | 3/1994 |
| JP | 6-296638 | | 10/1994 |
| JP | 9-299398 | | 11/1997 |
| JP | 11-107007 | | 4/1999 |
| JP | 11-140705 A | * | 5/1999 |
| JP | 11-140706 A | * | 5/1999 |
| JP | 2001-157693 A | * | 6/2001 |
| JP | 2002-320639 A | * | 11/2002 |

OTHER PUBLICATIONS

Machine translation of Japanese Patent Publication 09-299398.*
Machine translation of Japanese Patent Publication 06-296638.*
Machine translation of Japanese Patent Publication 06-054878.*

* cited by examiner

*Primary Examiner*—Jeff H. Aftergut
(74) *Attorney, Agent, or Firm*—Lowe Hauptman & Berner LLP

(57) ABSTRACT

A process includes feeding first and second webs and waist elastic members in a machine direction; joining the elastic members to the first and second webs and joining the webs to each other; joining to the first web; coating the first and second adhesive zones with adhesives; joining the second web folded inward in a cross direction to the first web and the panel in vicinities of transversely opposite side edges; successively cutting away transversely middle zones of the composite web along first cutting lines and folding the composite web together with the panel inward in the cross direction; and bonding respective halves of the composite web thus folded to each other in vicinities of second cutting lines and cutting the composite web together with the elastic members along the second cutting lines to make a plurality of the diapers.

13 Claims, 10 Drawing Sheets

PROCESS FOR MAKING A DISPOSABLE DIAPER

RELATED APPLICATIONS

The present application is based on, and claims priority from, Japanese Application Serial Number 2002-358465, filed Dec. 10, 2002, the disclosure of which is hereby incorporated by reference herein in its entirety.

BACKGROUND OF THE INVENTION

The present invention relates to a process for making a disposable diaper for absorption and containment of bodily discharges.

A process for making a disposable diaper has already been proposed in Japanese Patent Application Publication No. 1999-107007A. In this process, a continuous composite web is fed under a tension in a machine direction while a plurality of liquid-absorbent laminated panels each extending in a cross direction are fed at regular intervals in the machine direction onto an inner surface of the composite web and successively joined to the composite web.

More specifically, the process disclosed in the above-cited Publication comprises the steps of cutting transversely middle zones away from a continuous composite web along first cutting lines each describing a substantially circle to form a plurality of leg-holes spaced one from another by a given distance in the machine direction, placing the liquid-absorbent laminated panels on the continuous composite web and joining them to the composite web so that each of the liquid-absorbent laminated panels may be interposed between each pair of the adjacent leg-holes, and folding the composite web together with the panels along a longitudinal center line in two sections opposed to each other, joining the two sections opposed to each other in the vicinity of second cutting lines extending in the cross direction on both sides of each of the first cutting lines and then cutting the composite web along the second cutting lines to obtain a plurality of diapers arranged in the machine direction.

The composite web comprises a first web and a second web. The first web and the second web are overlapped together and respectively have inner surfaces opposed to and joined to each other by means of adhesives. Continuous waist elastic members extending in the machine direction and continuous leg elastic members extending in the cross direction are attached in a stretched state to the composite web. Specifically, the waist elastic members are attached to the composite web along its transversely opposite lateral zones. The leg elastic members are attached to the composite web between each pair of adjacent leg-holes formed through the composite web. The elastic members are interposed between the first web and the second web and attached to the webs by means of adhesives. In the diaper made by this process, the waist-surrounding upper end zone is defined by the transversely opposite side edge zones of the composite web.

According to the process disclosed in the above-cited Publication, the composite web comprises a pair of webs (i.e., the first web and the second web) placed upon each other along the transversely opposite lateral zones. Consequently, depending on a stretch ratio of the waist elastic members interposed between the webs, a contractile force of the waist elastic members remarkably act on the transverse opposite lateral zones of the composite web as the waist elastic members contract in the machine direction. In the individual diapers made by this process, therefore, the contractile force of the waist elastic members causes the waist-surrounding upper end zone defined by the transversely opposite side edge zones of the composite web to be formed with a plurality of crape-like irregular gathers. The crape-like gathers formed along the waist-surrounding upper end zone may be pressed against a wearer's skin and leave a compression mark on the skin. Such gathers may create a feeling of discomfort against the skin.

SUMMARY OF THE INVENTION

In view of the problem mentioned above, it is an object of the present invention to provide a process for making a disposable diaper improved so that the formation of gathers on a skin-contactable surface of the waist-surrounding upper end zone may be prevented and no feeling of discomfort against the skin may be experienced by a wearer.

The object set forth above is achieved by an improvement in the process for making a disposable diaper formed from a composite web and a liquid-absorbent laminated panel attached to an inner side of the composite web.

The improvement according to the present invention comprises the steps of: feeing a continuous first web and a continuous second web having a transverse dimension larger than a corresponding dimension of the first web in a machine direction under tension in the machine direction while feeding continuous waist elastic members stretched at a predetermined ratio in the machine direction so as to be laid along transversely opposite side edges of the first web; placing the first and second webs upon each other so that transversely opposite side edges of the second web extend outwardly of the transversely opposite side edges of the first web, then attaching the elastic members to an inner surface of at least one of the first and second webs and joining the first and second webs each other to form a composite web; placing a plurality of the panels each extending in a cross direction on the first web at regular intervals in the machine direction and joining to the first web; folding zones of the second web extending outwardly of the transversely opposite side edges of the first web inward in the cross direction along the side edges of the first web and joining the folded zone of the second web to the first web and to end zones of the panel in the cross direction; cutting transversely middle zones of the composite web each extending between each pair of the panels which is adjacent to each other along each of first cutting lines generally describing a circle and folding the composite web inward together with the panels in the cross direction along the machine direction with the panels lying inside; and joining respective halves of the composite web folded inward together in a vicinity of each of second cutting lines extending in the cross direction on both sides of the first cutting line and cutting the composite web together with the elastic members along the second cutting lines to form a plurality of the diapers arranged in the machine direction.

According to one preferred embodiment of the present invention, the process further includes coating first adhesive zones each continuously extending in the machine direction along each of the transversely opposite side edges of the second web on an inner surface of the second web with adhesives while coating second adhesive zones extending in the machine direction so as to be spaced one from another by a predetermined dimension in the machine direction and lying between the first adhesive zones and the adjacent side edges of the first web with adhesives, respectively, on the inner surface of the second web, and joining the inner surface of the second web to an outer surface of the first web and the zones of the panel extending in vicinities of its transversely opposite ends by means of adhesives applied on the first and second adhesive zones.

According to another preferred embodiment of the present invention, the process further includes coating first adhesive zones each continuously extending in the machine direction inside each of the transversely opposite side edges of the first web along each of the transversely opposite ends of the panel on the outer surface of the first web with adhesive while coating second adhesive zones extending in the machine direction so as to be spaced one from another by a predetermined dimension in the machine direction and extending in the cross direction from the first adhesive zones to the adjacent side edges of the first web, respectively, on the outer surface of the first web, and lying between the first adhesive zone and the adjacent side edge of the first web, and joining the inner surface of the second web to the outer surface of the first web and the zones of the panel extending in vicinities of its transversely opposite ends by means of adhesives applied on the first and second adhesive zones.

According to still another preferred embodiment of the present invention, each of the adhesive zones is laid between each pair of the panels which are adjacent to each other in the machine direction.

According to further another preferred embodiment of the present invention, the liquid-absorbent laminated panel comprises a liquid-absorbent core, a liquid-pervious topsheet covering an upper surface of the core and a liquid-impervious backsheet covering a lower surface of the core or comprises the liquid-absorbent core and at least the topsheet.

DETAILED DESCRIPTION OF THE PREFERRED EMBODIMENTS

Details of a process according to the present invention for making a disposable mentioned above will be more fully understood from the description given hereunder with reference to the accompanying drawings.

Figure 1:
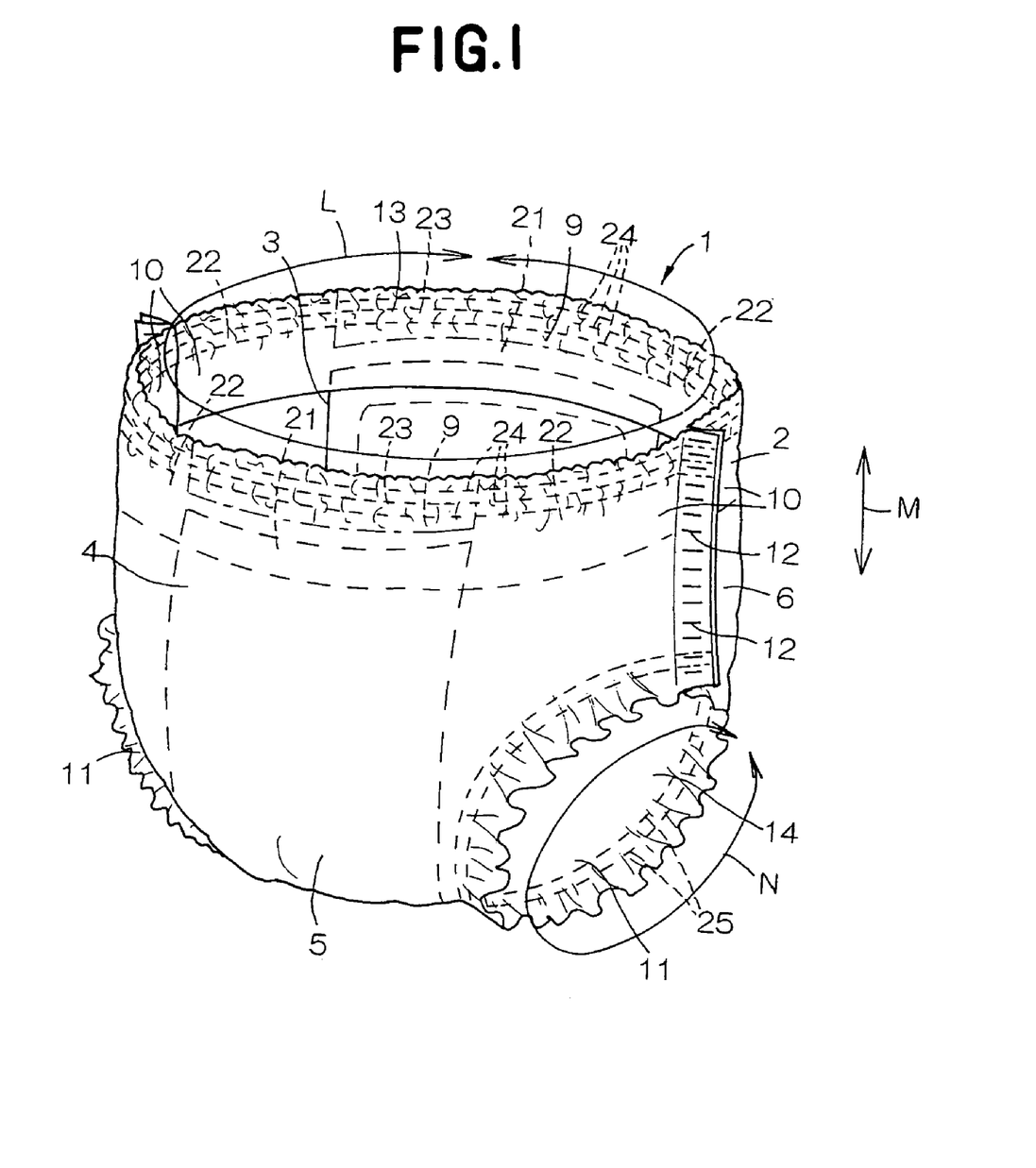
FIG. 1 is a perspective view showing a first embodiment of a diaper made by a process according to the present invention.
Figure 2:
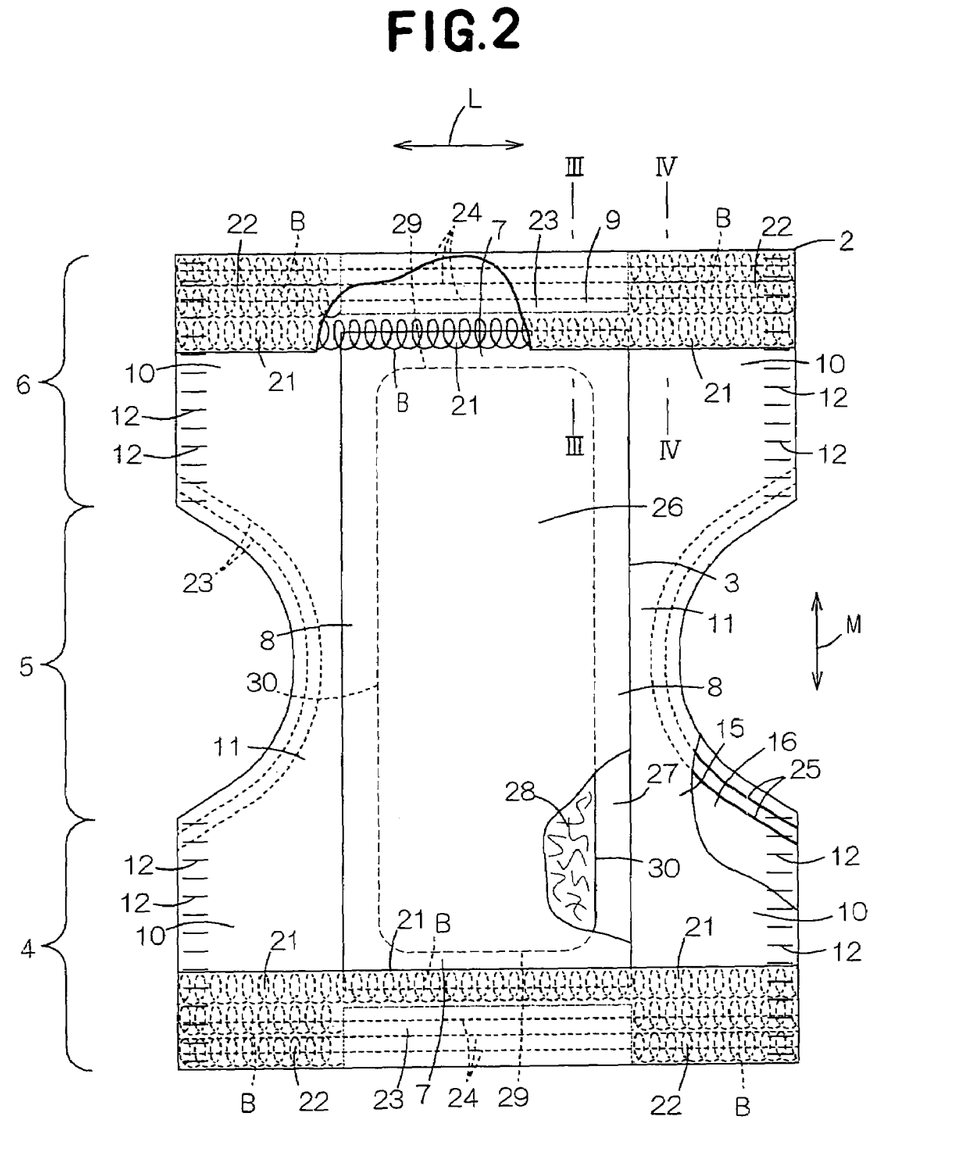
FIG. 2 is a developed plan view showing the diaper of FIG. 1 as partially broken away.
Figure 3:
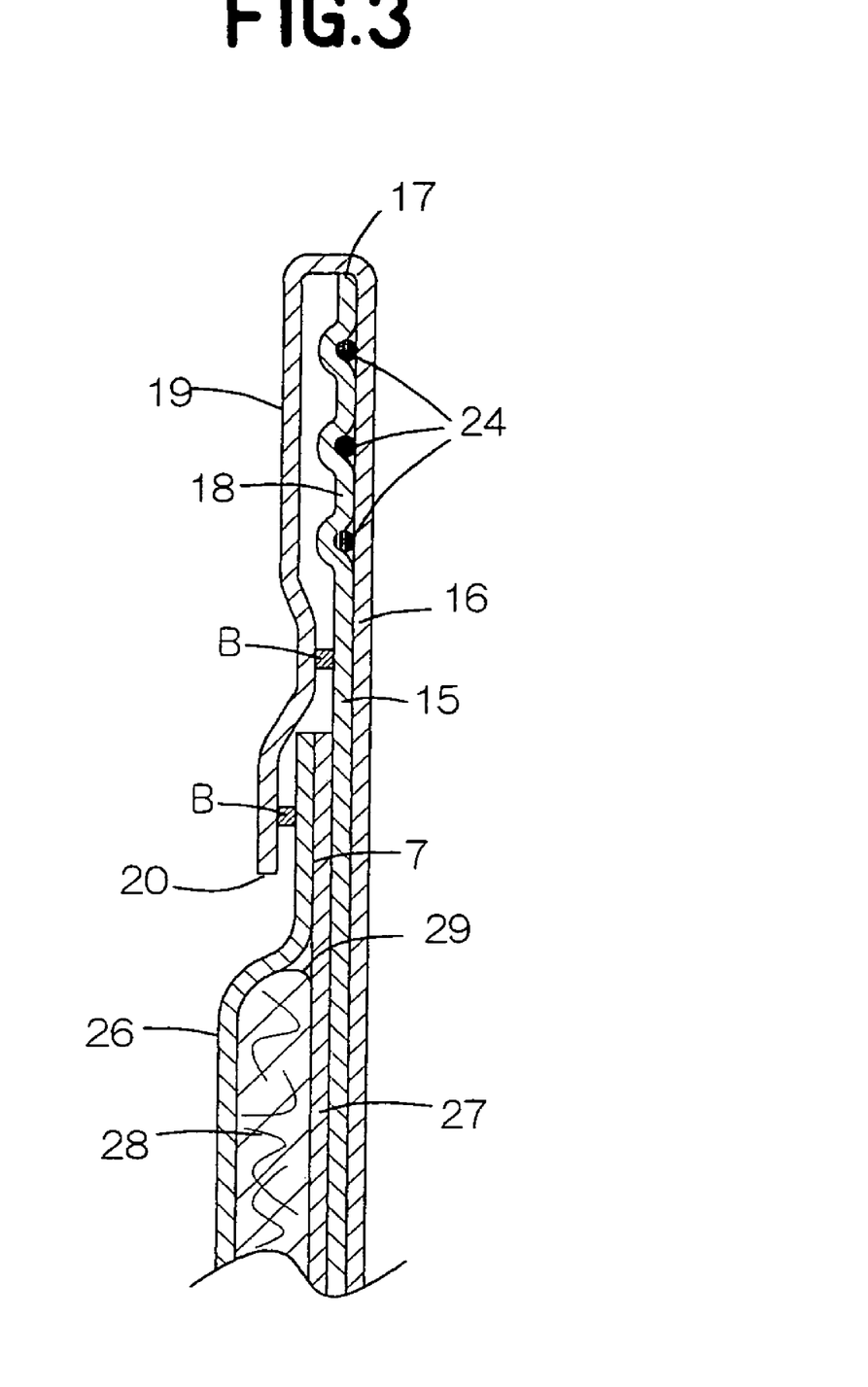
FIG. 3 is a sectional view taken along a line III—III in FIG. 2.
Figure 4:
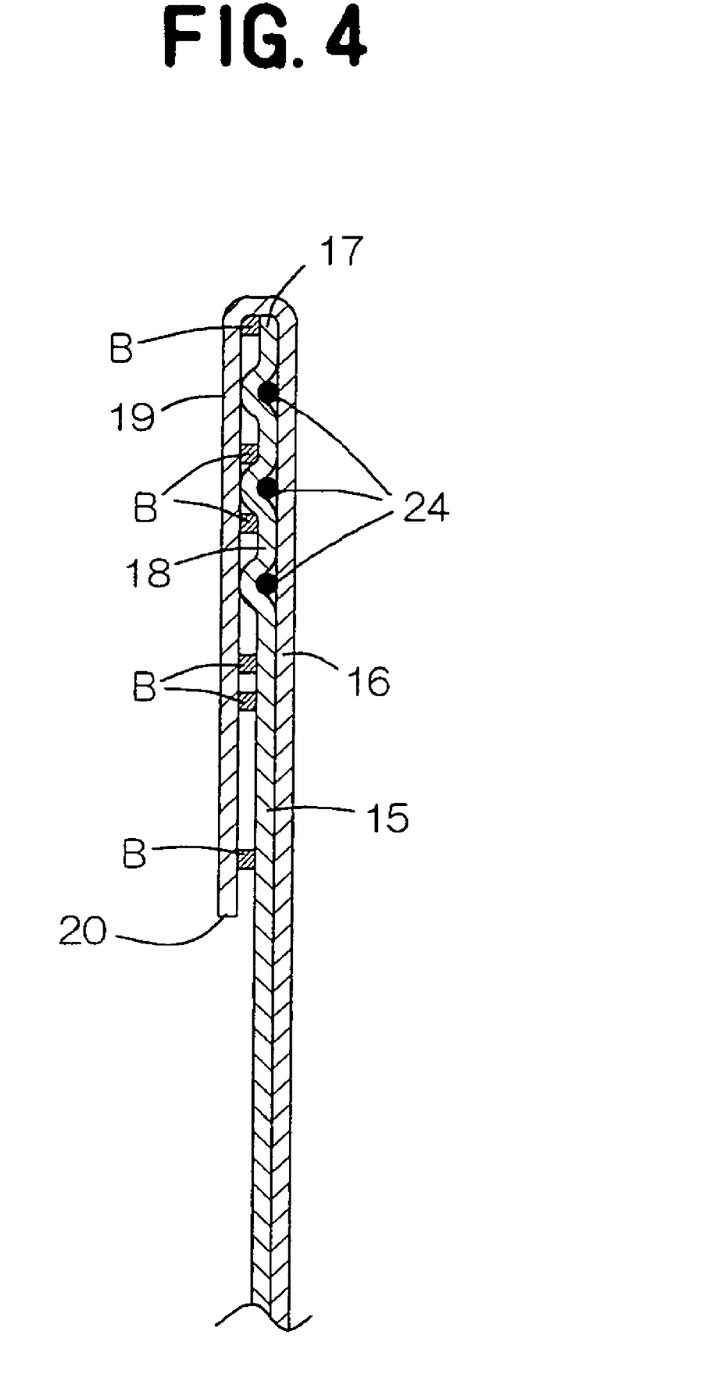
FIG. 4 is a sectional view taken along a line IV—IV in FIG. 2.

FIG. 1 is a perspective view showing a first embodiment of a diaper 1 made by a process according to the present invention, FIG. 2 is a developed plan view showing the diaper of FIG. 1 with front and rear waist regions 4, 6 disconnected from each other, as partially broken away, FIG. 3 is a sectional view taken along a line III—III in FIG. 2 and FIG. 4 is a sectional view taken along a line IV—IV in FIG. 2. In FIGS. 1 and 2, a waist-surrounding direction is indicated by an arrow L, a longitudinal direction is indicated by an arrow M and a leg-surrounding direction is indicated by an arrow N (in FIG. 1 alone).

A diaper 1 comprises a composite web 2 facing away from a wearer's skin and a liquid-absorbent laminated panel 3 attached to an inner surface of the composite web 2. The diaper 1 has the front waist region 4 and the rear waist region 6 opposed to each other and a crotch region 5 extending between these waist regions 4, 6.

The diaper 1 is contoured by a waist-surrounding upper end zone 9 lying outside longitudinally opposite end zones 7 of the panel 3 so as to extend in the front and rear waist regions 4, 6 in a waist-surrounding direction, waist regions' lateral zones 10 lying outside transversely opposite side edge zones 8 of the panel 3 so as to extend in the front and rear waist regions 4, 6 in a longitudinal direction and crotch region's lateral zones 11 lying outside the transversely opposite side edge zones 8 of the panel 3 so as to extend in the crotch region 5 in a leg-surrounding direction. As will be seen in FIG. 2, the crotch region's lateral zones 11 describe circular arcs which are convex inward as viewed in the waist-surrounding direction of the diaper 1. The diaper 1 has a generally hourglass-like planar shape in its developed state.

The lateral zones 10 of the respective waist regions are overlapped and joining together by means of a plurality of heat-sealing lines 12 arranged along the lateral zones 10 intermittently in the longitudinal direction. A waist-hole 13 is defined by the waist-surrounding upper end zone 9 and a pair of leg-holes 14 are respectively defined by the crotch region's lateral zones 11.

The composite web 2 comprises a first web 15 and a second web 16 underlying the first web 15. The first web 15 and the second web 16 are intermittently joined together by means of adhesives (not shown) applied on at least one of these first and second webs 15, 16. As viewed in the diaper 1, the second web 16 has a dimension measured in the longitudinal direction larger than a dimension of the first web 15 measured in the corresponding direction. Marginal zones 19 of the second web 16 extending outwardly beyond longitudinally opposite edges 17 of the first web 15 so as to extend along the respective edges 17 of the first web 15 are folded back along the ends 17 of the first web 15 onto an inner side of the diaper 1.

The marginal zones 19 of the second web 16 are joined to transversely opposite end zones 18 of the first web 15 and to longitudinally opposite end zones 7 of the panel 3 by means of first adhesive zones 21 and second adhesive zones 22, respectively. Each of the first adhesive zones 21 continuously extends in the waist-surrounding direction along the edge zones 20 of the second web 16, in other words, continuously extends in the waist-surrounding direction on a section of the first web 15 defined inside vicinities of the edge zones 20. Each of the second adhesive zones 22 is define in each of the waist regions' lateral zones 10 and extends from the associated first adhesive zone 21 and the edge zone 17 of the first web 15.

The first and second adhesive zones 21, 22 are coated with adhesives B in spiral pattern. Non-adhesive zones 23 coated with no adhesives are defined outwardly of the outer end zones 7 of the panel 3 between respective pairs of the second adhesive zones 22 which are adjacent in the waist-surrounding direction. In the non-adhesive zones 23, the end zones 18 of the first web 15 are not joined to the end zones 19 of the second web 16, in other words, the end zones 18, 19 are left free one from another.

The waist-surrounding upper end zone 9 is provided along the waist-hole 13 with a plurality of waist elastic members 24 extending in a waist-surrounding direction and contractibly attached thereto. The waist elastic members 24 are pass through the second adhesive zones 22 and the non-adhesive zones 23. The crotch region's lateral zones 11 are provided along the respective leg-holes 14 with a plurality of leg elastic members 25 extending in a leg-surrounding direction and contractibly attached thereto. The waist elastic members 24 and the leg elastic members 25 are interposed between the first and second webs 15, 16 and intermittently joined to these webs 15, 16 by means of adhesives (not shown).

The panel 3 has its area smaller than the area of the composite web 2 and a rectangular shape which is relatively long in the longitudinal direction. The panel 3 extends over the crotch region 5 further into the front and rear waist regions 4, 6. The panel 3 comprises a liquid-pervious topsheet 26 facing a wearer's skin, a liquid-impervious backsheet 27 facing away from a wearer's skin and a liquid-absorbent core 28 interposed between the top- and backsheets 26, 27. The core 28 has its upper surface entirely covered with the topsheet 26 and its lower surface entirely covered with the backsheet 27. The core 28 is intermittently joined to the upper and lower surfaces by means of adhesives (not shown).

The longitudinally opposite end zones 7 of the panel 3 are defined by portions of the top- and backsheets 26, 27 extending outwardly beyond longitudinally opposite ends 29 of the core 28 in the longitudinal direction and the transversely opposite side edge zones 8 of the panel 3 are defined by portions of the top- and backsheets 26, 27 extending outwardly beyond transversely opposite side edges 30 of the core 28 in the transverse direction. Along the longitudinally opposite end zones 7 and the transversely opposite side edge zones 8 of the panel 3, the top- and backsheets 26, 27 are overlaid and joined together. The backsheet 27 constituting the panel 3 is joined to the first web 15 by means of adhesives (not shown).

The waist-surrounding upper end zone 9 of the diaper 1 is formed from three layers defined by the second web 16 folded in two and the transversely opposite end zones 18 of the first web 15 interposed between the second web 16 folded in two. When the diaper 1 is worn, the end zones 19 of the second web 16 extending in the waist-surrounding direction on an inner side of the diaper 1 directly contact a wearer's skin. Even when the elastic members 24 contract in the transverse direction and a contractile force thereof acts upon the end zones 19 of the second web 16, the end zones 18 of the first web 15 interposed between the end zones 19 of the second web 16 and the waist elastic members 24 function to alleviate an anxiety due to such contractile force that the crape-like gathers might be formed on the end zones 19 of the second web 16. Particularly because the respective end zones 18, 19 of the first and second webs 15, 16 are left free one from another in the non-adhesive zones 23, the contractile force of the elastic members 24 insufficiently acts upon the end zones 19 of the second web 16 to form the end zones 19 with a plurality of crape-like gathers. In this way, it is unlikely that any compression mark might be left on the skin and a wearer might experience a feeling of discomfort against the skin during the end zones 10 of the second web 16 being in contact with the skin of a wearer.

The panel 3 may be formed with the liquid-pervious topsheet 26 and the liquid-absorbent core 28. In this case, the core 28 and the topsheet 26 lying on the end zones 7 as well as the side edge zones 8 of the panel 3 are joined to the first web 15 by means of adhesives (not shown).

Figure 5:
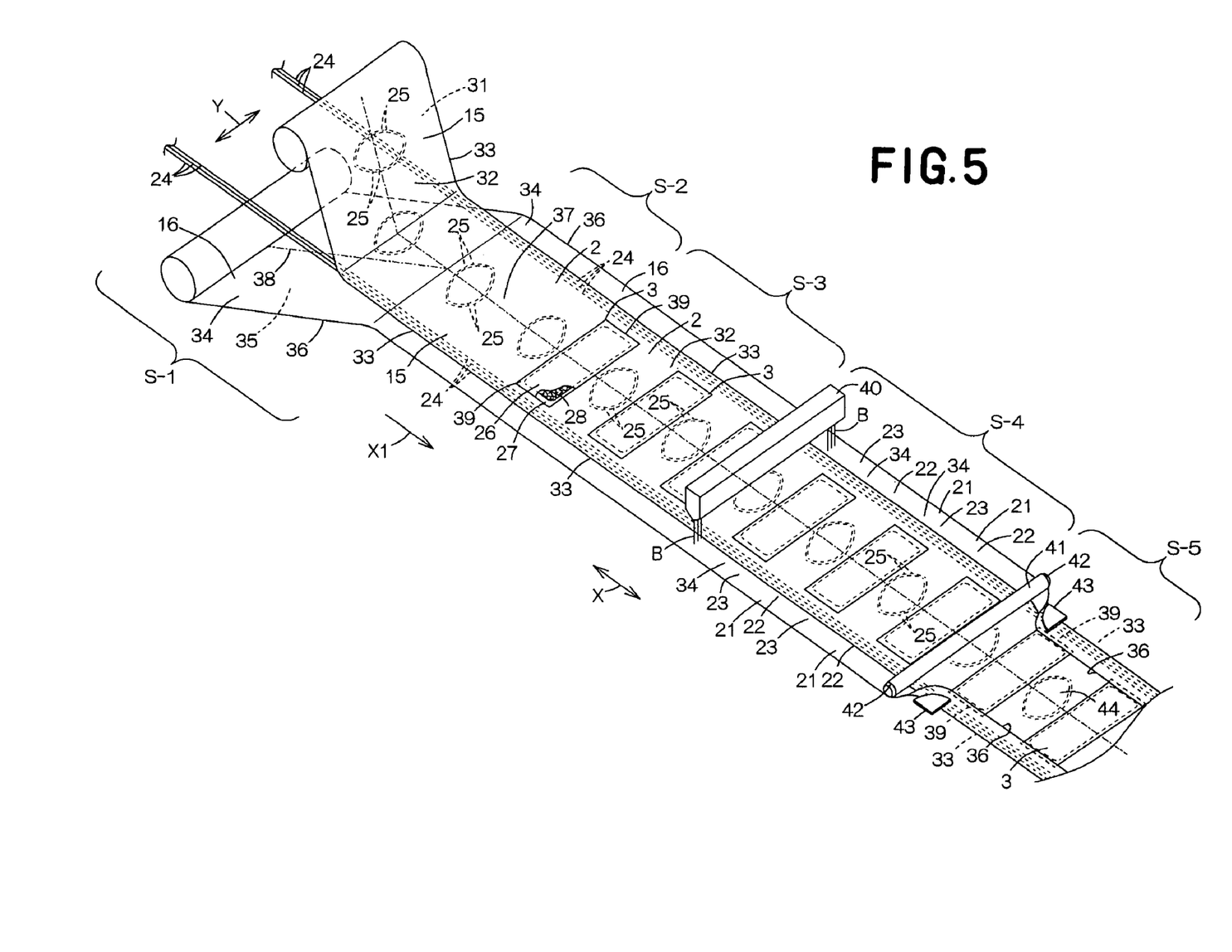
FIG. 5 is a perspective view illustrating several steps of the process according to the first embodiment of the present invention.
Figure 6:
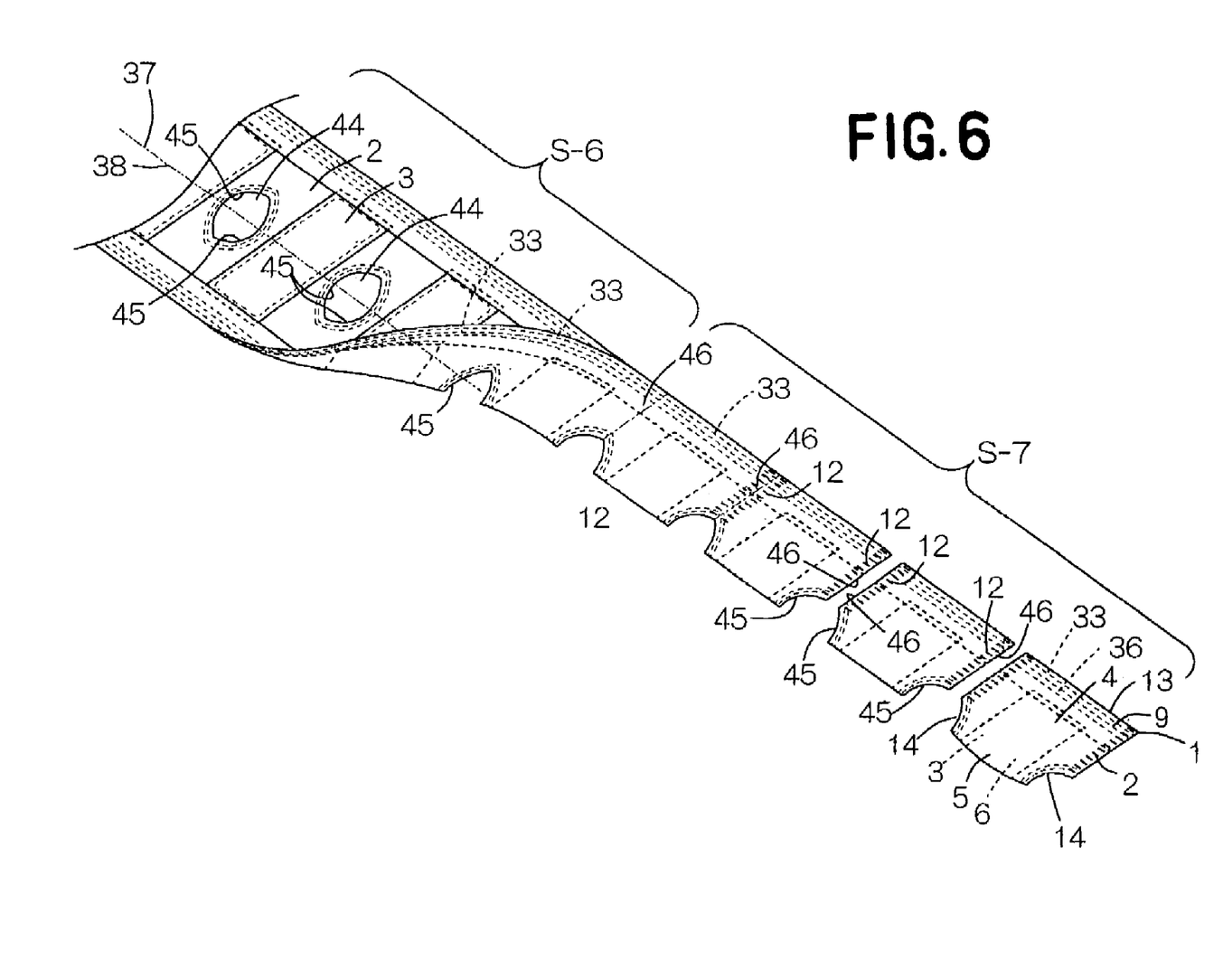
FIG. 6 is a perspective view illustrating the steps subsequent to the steps illustrated by FIG. 5.
Figure 7:
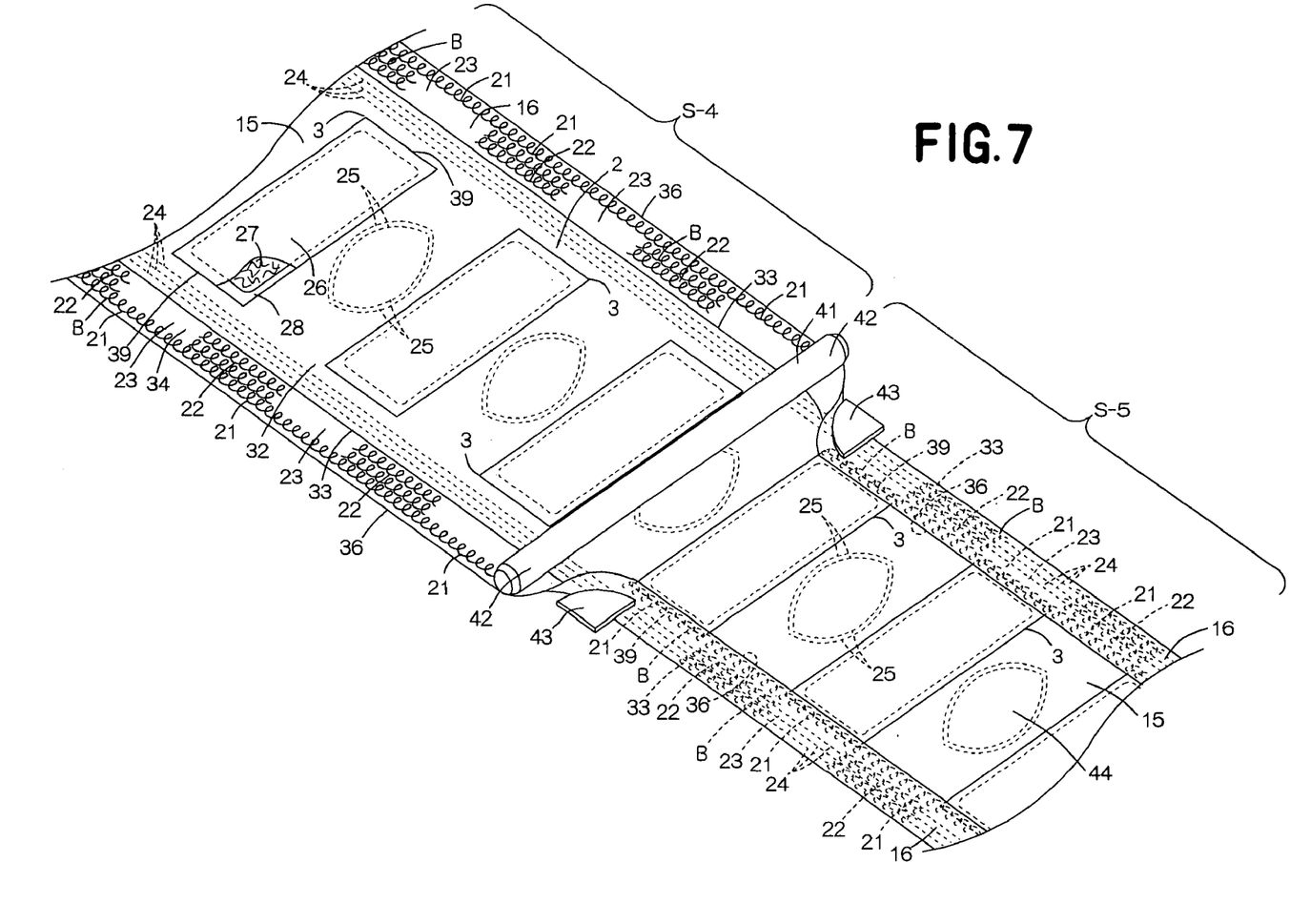
FIG. 7 is a perspective view illustrating, in enlarged scale, an adhesive coating step and a web joining step.

FIG. 5 is a perspective view illustrating several steps of a process according to the first embodiment of the present invention for making the disposable diaper 1, FIG. 6 is a perspective view illustrating the steps subsequent to the steps illustrated by FIG. 5 and FIG. 7 is a perspective view illustrating, in enlarged scale, a step S-4 and a step S-5. In FIGS. 5 and 6, a machine (longitudinal) direction is indicated by an arrow X and a cross (transverse) direction is indicated by an arrow Y. The wording "inner surfaces 31, 34 of the first and second webs 15, 16" refers to surfaces of the webs 15, 16 facing to each other and the wording "outer surfaces 32, 35 of the webs 15, 16" refers to the surfaces of the webs 15, 16 facing away from respective inner surfaces 31, 34 of the webs 15, 16.

Basically, a process according to the present invention for making the disposable diaper 1 comprises the steps of: (1) feeding continuous waist elastic members 24 in the machine direction while feeding a continuous first web 15 and a continuous second web 16 in the machine direction (step S-1); (2) joining the elastic members 24 to the first and second webs 15, 16 and joining the webs 15, 16 to each other (step S-2); (3) joining the panel 3 to the first web 15 (step S-3); (4) coating the first and second adhesive zones 21, 22 with adhesives B (step S-4); (5) joining the second web 16 folded inward in the cross direction to the first web 15 and the panel 3 by means of adhesives B in vicinities of opposite side edges 36 of the second web 16 (step S-5); (6) successively cutting away transversely middle zones 44 of the composite web 2 along each of first cutting lines 45 and folding the composite web 2 together with the panel 3 inward in the cross direction (step S-6); and (7) joining respective halves of the composite web 2 thus folded to each other in vicinities of each of second cutting lines 46 and cutting the composite web 2 together with the elastic members 24 along each of the second cutting lines 46 to make a plurality of the diapers 1 arranged in the machine direction (step S-7).

It should be noted that the continuous first web 15 and the continuous second web 16 correspond to the first web 15 and the second web 16, respectively, of the diaper 1 shown in FIG. 1. Similarly, the continuous waist elastic members 24 correspond to the waist elastic members 24 of the diaper 1 shown in FIG. 1. The respective steps S-1 through S-7 of the process will be described in more details.

In a step S-1, the continuous first web 15 and the continuous second web 16 are continuously fed in the machine direction and a plurality of the continuous waist elastic members 24 are fed also in the machine direction. The first and second webs 15, 16 as well as the waist elastic members 24 are fed forward in the machine direction X1 at a predetermined velocity using rotational force of a pair of nip rollers (not shown) and/or a drive roller (not shown) provided in operative association with the webs 15, 16. The first and second webs 15, 16 are always drawn forward in the machine direction without being slackened in the machine direction.

The first web 15 has an inner surface 31 and an outer surface 32 and transversely opposite side edges 33 extending in the machine direction. The first web 15 is provided on its inner surface 31 with a plurality of the leg elastic members 25 attached in a stretched state. The elastic members 25 are arranged so as to be spaced one from another by a given dimension in the machine direction. The elastic members 25 may be attached to the first web 15 by means of adhesives (not shown) applied on the inner surface 31 of the first web 15 or on the elastic members 24.

The second web 16 has an inner surface 34 and an outer surface 35 and transversely opposite side edges 36. A transverse dimension of the second web 16 defined between the side edges 36 is larger than the corresponding dimension of the first web 15. The waist elastic members 24 are maintained at a predetermined stretch ratio while they are fed forward in the machine direction at a predetermined velocity. The elastic members 24 are laid between the first and second webs 15, 16 so as to extend in the machine direction immediately inside the transversely opposite side edges 33 of the first web 15.

In a step S-2, the inner surfaces 31, 34 of the first and second webs 15, 16 are placed upon each other so that respective longitudinal center lines 37, 38 of the webs. 15, 16 may fall into line and the webs 15, 16 are joined to each other to form the composite web 2. In the course of this step, the elastic members 24 are attached to at least one of the inner surfaces 31, 34 of the webs 15, 16. In the webs 15, 16 placed upon each other, the side edges 33 of the first web 15 lie inside the side edges 36 of the second web 16. Joining of the webs 15, 16 to each other as well as joining the elastic members 24 to the webs 15, 16 may be achieved by means of adhesives (not shown) intermittently applied on at least one of the inner surfaces 31, 34 of the webs 15, 16.

In a step S-3, a plurality of the liquid-absorbent panels 3 each being elongate in the cross direction are successively fed. After placed on the inner surface 32 of the first web 15 at regular intervals in the machine direction, the panels 3 are successively joined to the inner surface 32 of the first web 15. Each of the panels 3 is laid between each pair of the adjacent groups of the elastic members 25 and has transversely opposite end zones 39 laid immediately inside the side edges 33 of the first web 15.

The panel 3 comprises the liquid-absorbent core 28, the liquid-pervious topsheet 26 covering the entire upper surface of the core 28 and the liquid-impervious backsheet 27 covering the entire lower surface of the core 28. Along the end zones 7 as well as along the side edge zones 8, the top- and backsheets 26, 27 are overlapped and joined together. The backsheet 27 constituting the panel 3 is joined to the outer surface 32 of the first web 15. Joining of the panel 3 to the first web 15 may be achieved by means of adhesives (not shown) intermittently applied on at least one of the outer surface 32 of the first web 15 and the backsheet 27.

In a step S-4, the first adhesive zones 21 and the second adhesive zones 22 are coated by an adhesive coater head 40 with adhesives B. As will be seen in FIG. 7, the first adhesive zones 21 are defined on the inner surface 34 of the second web 16 and continuously extend in the machine direction along the side edges 36 of the second web 16. The second adhesive zones 22 are defined on the inner surface 34 of the second web 16 and intermittently extend in the machine direction and are spaced one from another by a given dimension, each of the second adhesive zones 22 being laid between the associated first adhesive zone 21 and the side edge 33 of the first web 15. The second adhesive zones 22 are also laid between each pair of the panels 3 which are adjacent to each other in the machine direction. The non-adhesive zones 23 coated with no adhesives B are defined between each pair of the second adhesive zones 22 which are adjacent to each other in the machine direction. The second adhesive zones 22 and the non-adhesive zones 23 are alternately arranged in the machine direction. Coating of the adhesives B is performed in a spiral pattern extending in the machine direction. Obviously, the patter in which the adhesives B is applied is not limited to the spiral pattern but the adhesives B may be applied in the other pattern such as a zigzag-pattern, a dot-pattern or a stripe-pattern.

In a step S-5, in vicinities of the side edges 36 of the second web 16, the second web 16 is folded inward in the cross direction along the side edges 33 of the first web 15 and the inner surface 34 of the second web 16 is joined to the inner surface 32 of the first web 15 and to the end zones 39 of the panel 3 by means of the adhesives B applied on the first and second adhesive zones 21, 22. The waist elastic members 24 extend to pass through the second adhesive zones 22 as well as the non-adhesive zones 23.

To fold the second web 16, a guide roller 41 provided in contact with the outer surface 32 of the first web and extending in the cross direction and a pair of guide metal fittings 43 provided immediately downstream of the guide roller 41 so as to be opposed to each other in the cross direction are used. The side edges 36 of the second web 16 is prevented by opposite end portions 42 of the guide roller 41 from being folded before the second web 16 come in contact with the guide metal fittings 43. Immediately after the second web 16 has passed the guide roller 41, the side edges 36 thereof come in contact with respective lower surfaces of the guide metal fittings 43 and thereupon the side edges 36 are folded toward center line 37, 38 in the cross direction.

According to this process, the first adhesive zones 21 extend along the side edges 36 of the second web 16 and the adhesives B is not present inside the side edges 36 having been folded inward in the cross direction. In other words, no adhesives B remain in the portions of the webs 15, 16 except for the zones in which the webs 15, 16 are joined together.

In a step S-6, each transversely middle zone 44 extending between each pair of the panels 3 which are adjacent to each other in the machine direction (i.e., zone surrounded by leg elastic members 25) of the composite web 2 is cut away along a first cutting line 45 generally describing a circle and then the composite web 2 is folded transversely inward together with the panels 3 along the center line 37, 38 with the panels 3 inside so that the transversely opposite side edges 33 of the first web 15 may fall into line. The transversely middle zone 44 of the composite web 2 may be cut away after the composite web 2 has folded transversely inward together with the panel 3 along the center line 37, 38.

According to this process, the first and second webs 15, 16 are joined to each other by means of adhesives B applied on the second adhesive zones 22, so stiffness of the webs 15, 16 in the second adhesive zones 22 is higher than when the zones 22 are not coated with adhesives B. According to this process, the second adhesive zones 22 intermittently arranged in the machine direction function to alleviate an influence of the waist elastic members 25 upon the side edges 33, 36 of the webs 15, 16 even when a contractile force of the elastic members 25 acts upon the side edges 33, 36 of the webs 15, 16.

If none of the second adhesive zones 22 is provided, a contractile force of the waist elastic members 25 will remarkably act upon the respective side edges 33, 36 of the first and second webs 15, 16. Consequently, the side edges 33, 36 of the first and second webs 15, 16 will be deformed in a tubular shape and/or deformed so as to undulate in the cross direction. If the side edges 33, 36 of the webs 15, 16 are deformed in this manner, it will be impossible to fall the side edges 33 of the first web 15 into line when the composite web 2 is folded together with the panels 3 along the center lines 37, 38 inward in the cross direction. That is, the side edges 33 may often shift from each other.

According to this process, the side edges 33, 36 of the webs 15, 16 are substantially not affected by the contractile force of the waist elastic members 25 and substantially not deformed. In other words, it is ensured that the side edges 33 can reliably brought into line when the composite web 2 is folded together with the panels 3 along the center lines 37, 38 without any fear that the side edges 33 of the first web 15 might shift from each other.

In a step S-7, the two sections opposed to each other of the composite web 2 folded in two are joined together in vicinities of the second cutting lines 46 extending on both sides of each of the first cutting lines 45 in the cross direction whereupon the composite web 2 is cut along the second cutting lines 46. A plurality of the diapers 1 (See FIG. 1) arranged in the machine direction are made. The sections opposed to each other of the composite web 2 folded in two are joined together by means of a plurality of heat-sealing lines 12 lying on both sides of the respective second cutting lines 46 as viewed in the machine direction and arranged intermittently in the cross direction.

The diaper 1 made by this process has the front and rear waist regions 4, 6, the crotch region 5 extending between the waist regions 4, 6, the waist-hole 13 defined by the waist-surrounding upper end zone 9 and a pair of the leg-holes 14 defined by the respective crotch region's lateral zones 11. The waist-surrounding upper end zone 9 is defined by zones extending along the side edges 33, 34 of the first and second webs 15, 16.

The waist-surrounding upper end zone 9 of the diaper 1 is formed by three layers defined by the second web 16 folded in two and the first web 15 interposed between the second web 16 folded in two (See FIGS. 3 and 4). In the case of this diaper 1, even if the contractile force of the waist elastic members 24 acts upon the second web 16, an influence of such contractile force will be not so remarkable to form the second web with gathers. In the non-adhesive zones 23, the side edges 33, 34 of the first and second webs 15, 16 are left free from each other the contractile force of the elastic members 24 scarcely acts upon the side edge zones 34 of the second web 15, so it is unlikely that the side edge zones might be formed with a plurality of crape-like gathers. In this way, this process allows the disposable diapers 1 having the waist-surrounding upper end zone 9 free from such undesirable gathers and offering a comfortable feeling to wear to be continuously made.

Figure 8:
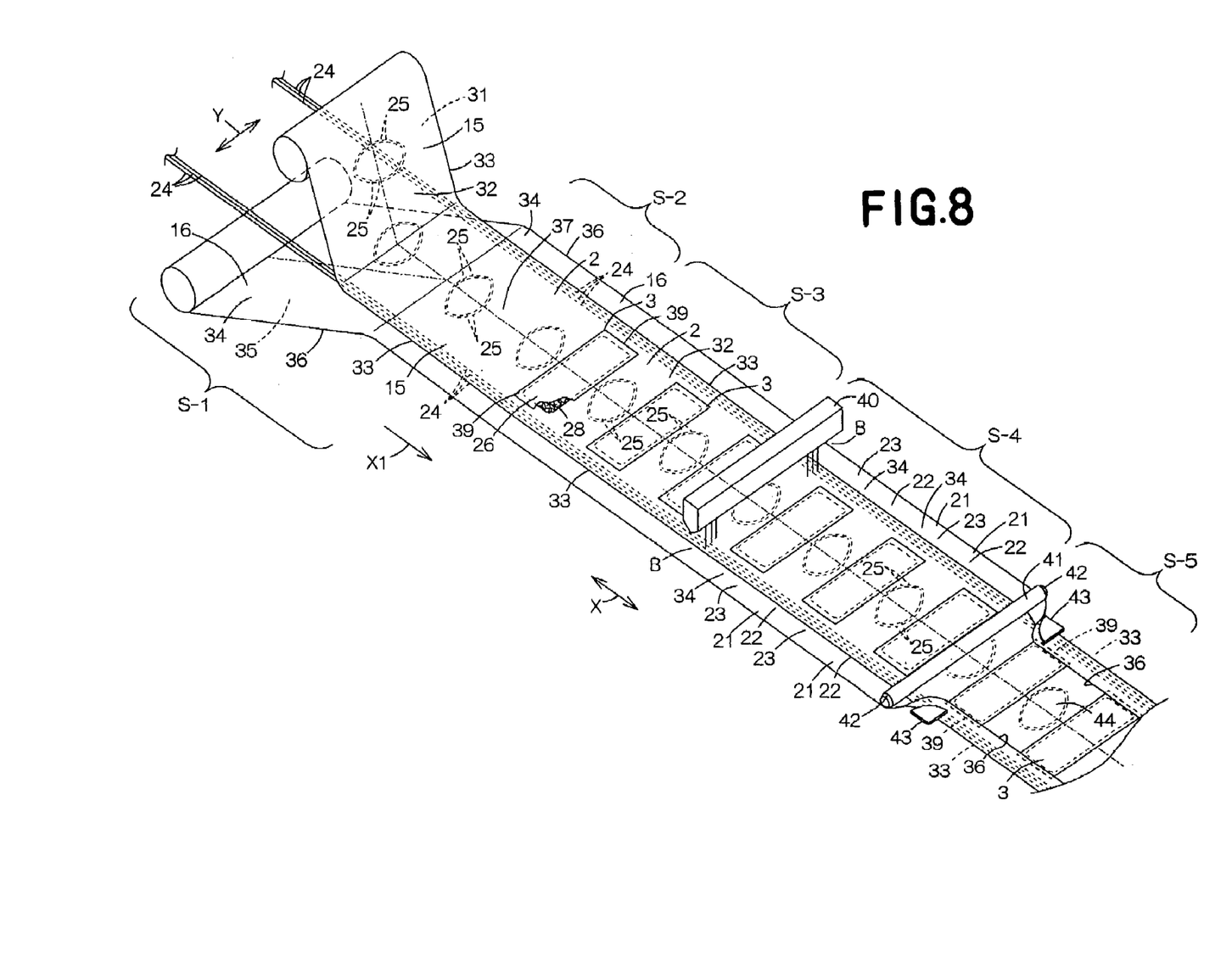
FIG. 8 is a perspective view illustrating several steps of the process according to a second embodiment of the present invention.
Figure 9:
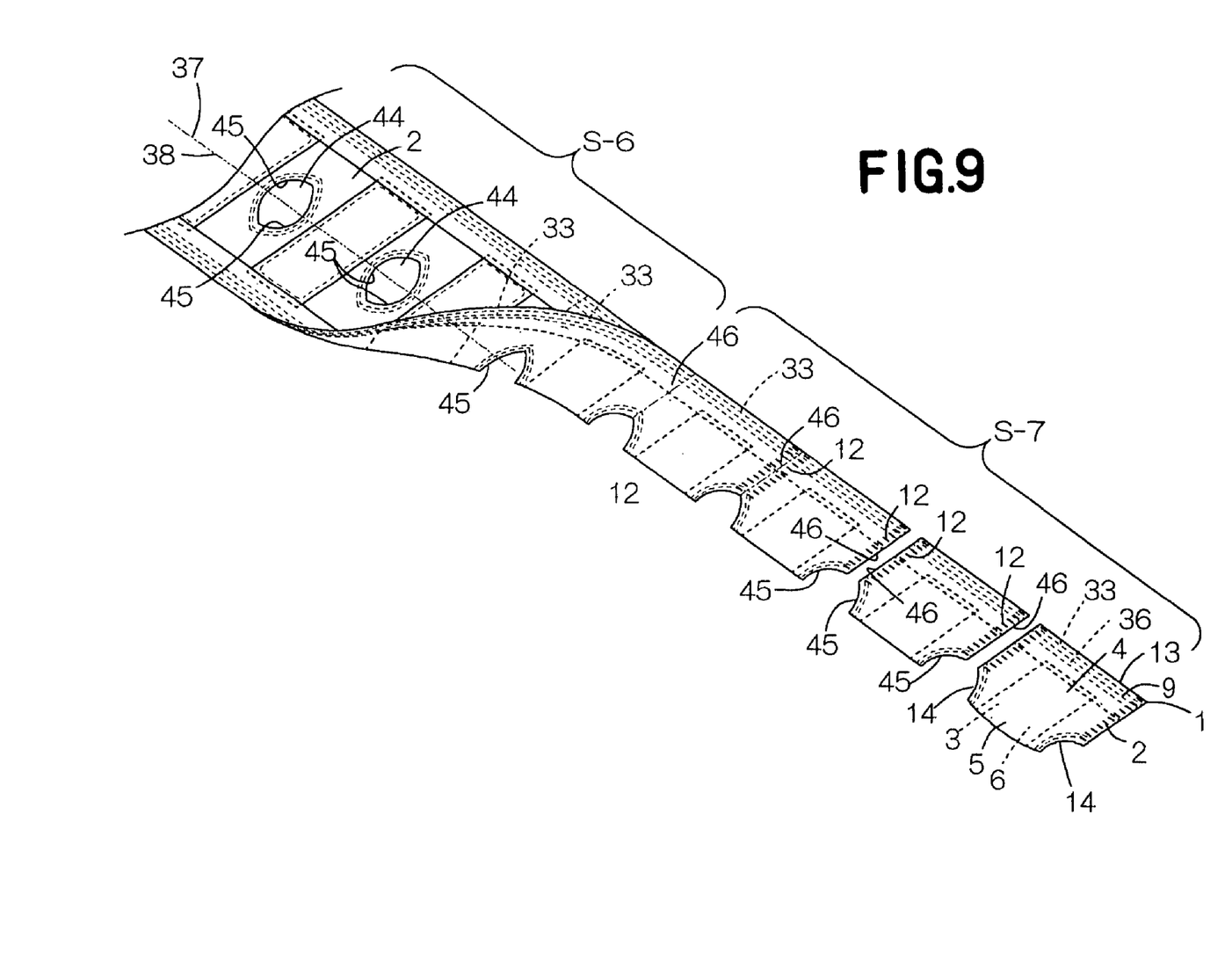
FIG. 9 is a perspective view illustrating the steps subsequent to the steps illustrated by FIG. 8.
Figure 10:
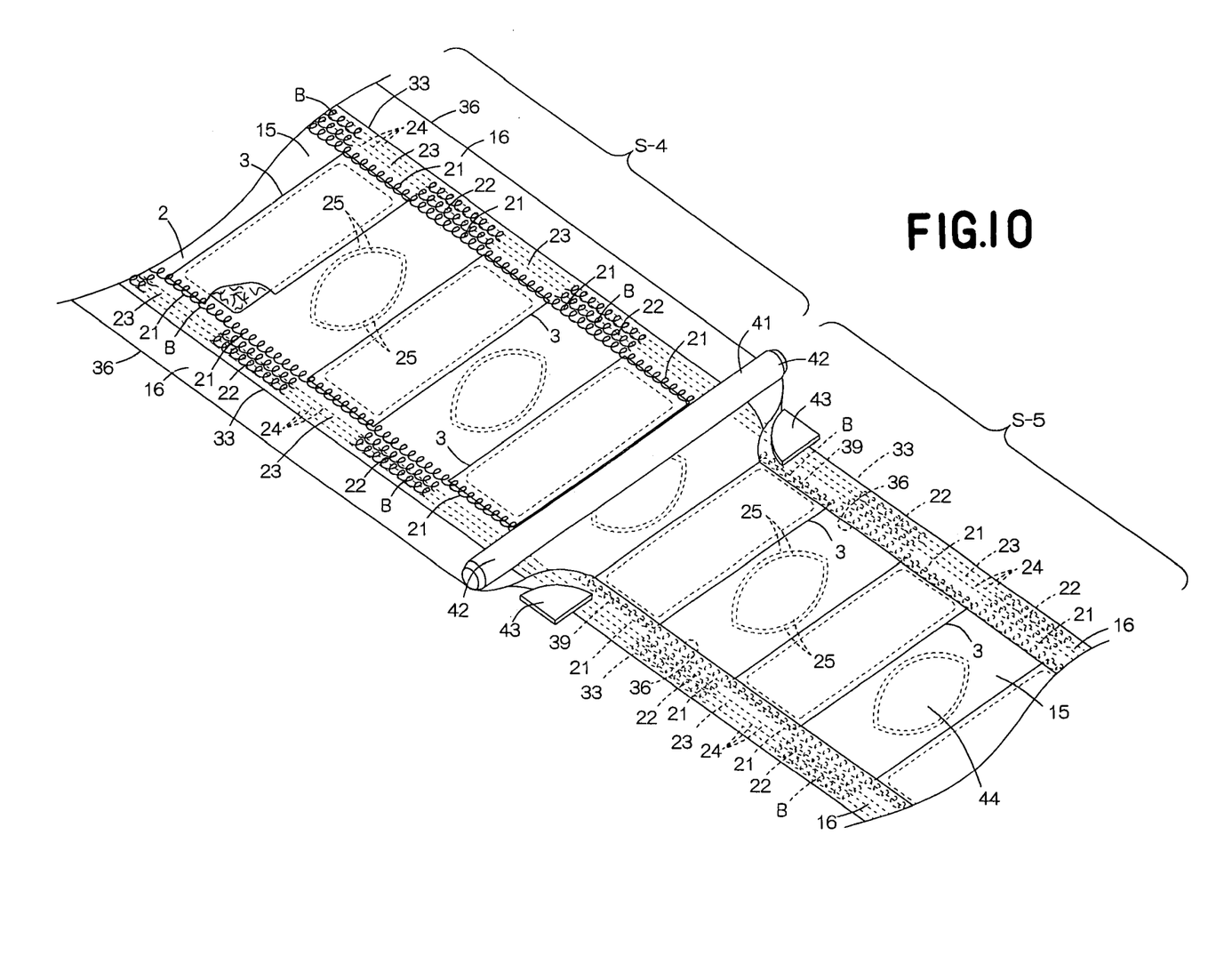
FIG. 10 is a perspective view illustrating, in enlarged scale, an adhesive coating step and a web joining step.

FIG. 8 is a perspective view illustrating several steps of the process according to a second embodiment of the present invention, FIG. 9 is a perspective view illustrating the steps subsequent to the steps illustrated in FIG. 8 and FIG. 10 is a perspective view illustrating, in enlarged scale, a step S-4 and a step S-5.

The second embodiment is similar to the first embodiment previously described except for the backsheet 27 of the panel 3 and a step S-4, where steps and components similar to those of the first embodiment have the same signs and the description thereof is omitted to avoid it repeat. As will be seen in FIG. 10, unlike the first embodiment, the panel 3 comprises the liquid-absorbent core 28 and the liquid-pervious topsheet 26 covering the entire upper surface of the core 28. In a step S-4 of the second embodiment, the first adhesive zones 21 are defined on the outer surface 32 of the first web 15 and continuously extend in the machine direction inside the transversely opposite side edges 33 of the first web 15, and the second adhesive zones 22 are formed on the outer surface 32 of the first web 15 and intermittently extend in the machine direction and are spaced one from another by a given dimension, each of the second adhesive zones 22 being laid between the associated first adhesive zone 21 and the adjacent side edge 33 of the first web 15. The non-adhesive zones 23 coated with no adhesive B are formed between each pair of the second adhesive zones 22 which are adjacent to each other in the machine direction. The second adhesive zones 22 and the non-adhesive zones 23 are alternately arranged in the machine direction.

According to this process, the adhesive B applied on the second adhesive zones 22 serves to enhance stiffness of the webs 15, 16 in the second adhesive zones 22 and thereby to ensure that, when the contractile force of the waist elastic members 25 acts upon the webs 15, 16 in vicinities of the side edges 33, 36 thereof, such influence is effectively alleviated by the presence of the second adhesive zones 22. With a consequence, the side edges 33, 36 of the webs 15, 16 are substantially not affected by the contractile force of the waist elastic members 25 and substantially not deformed. In other words, it is ensured that the side edges 33 can reliably brought into line when the composite web 2 is folded together with the panels 3 along the center lines 37, 38.

The diaper 1 made by this process has the front and rear waist regions 4, 6, the crotch region 5 extending between these waist regions 4, 6, the waist-hole 13 defined by the waist-surrounding upper end zone 9 and a pair of the leg-holes 14 defined by the respective crotch region's lateral zones 11. The waist-surrounding upper end zone 9 is defined by zones extending along the side edges 33, 34 of the first and second webs 15, 16.

The waist-surrounding upper end zone 9 of the diaper 1 made using this process is formed by three layers defined by the second web 16 folded in two and the first web 15 interposed between the second web 16 folded in two. In this way, this process allows the disposable diapers 1 having the waist-surrounding upper end zone 9 free from such undesirable gathers and offering comfortable feeling to wear to be continuously made.

A stock material for the first and second webs 15, 16 may be selected from the group consisting of a hydrophobic fibrous nonwoven fabric, a breathable liquid-impervious plastic film, a composite nonwoven fabric comprising two hydrophobic fibrous nonwoven fabric layers laminated on each other and a composite sheet comprising a hydrophobic fibrous nonwoven fabric and a breathable liquid-impervious plastic film laminated on each other. The topsheet 26 may be formed from a hydrophilic fibrous nonwoven fabric. The backsheet 27 may be formed from a hydrophobic fibrous nonwoven fabric or a breathable liquid-impervious plastic film.

The fibrous nonwoven fabric may be selected from those obtained by spun lace-, needle punch-, melt blown-, thermal bond-, spun bond-, chemical bond- and air through-processes. The component fiber of the nonwoven fabric may be selected from the group consisting of polyolefin-, polyester- and polyamide-based fibers and core-sheath type or side-by-side type conjugate fiber of polyethylene/polypropylene or polyethylene/polyester. The plastic film is preferably formed from a polyolefin-based thermoplastic synthetic resin.

The core 28 comprises a mixture of fluff pulp and super-absorbent polymer particles or a mixture of fluff pulp, super-absorbent polymer particles and thermoplastic synthetic resin fibers, in both cases, compressed to a desired thickness. Preferably, the core 28 is entirely covered with a water-pervious sheet such as tissue paper in order to prevent the core from getting out of its initial shape and/or to prevent the polymer particles from falling off. The adhesive B may be selected from the group consisting of a hot melt adhesive, an acrylic adhesive and a rubber-based adhesive.

The process according to the present invention for making the disposable diaper is primarily characterized in that the zones of the second web extending along its transversely opposite side edges are folded inward in the cross direction along the transversely opposite side edges of the first web and the inner surface of the second web are joined to the outer surface of the first web and to the panel in vicinities of its longitudinally opposite ends. The process is also characterized in that the waist-surrounding upper end zone of the diaper made by this process is formed by three layers defined by the second web folded in two and the first web interposed between the second web folded in two. Therefore, even if the contractile force of the waist elastic members acts upon the waist-surrounding upper end zone, it is unlikely that the side edge zones might be formed with a plurality of crape-like gathers. In this way, this process allows the disposable diapers having the waist-surrounding upper end zone free from such undesirable gathers and offering a feeling of comfort against the skin of a wearer.

The process also makes it possible to make the diaper having its waist-surrounding upper end zone formed with the non-adhesive zones in which the first and second webs are not joined to each other. In these non-adhesive zones, the second web is substantially free from the influence of the waist elastic members' contractile force which otherwise would form the non-adhesive zones of the second web with gathers. The novel process thus allows the diaper having its waist-surrounding upper end zone which offers a comfortable touch and a high flexibility.

According to the embodiment of the process including the step of coating the first and second adhesive zones with adhesives, the second adhesive zones arranged intermittently in the machine direction serve to alleviate the contractile force of the waist elastic members which otherwise might deform the zones extending along the side edges of the respective webs. In this way, the transversely opposite side edges of the first web reliably fall into line as the composite web is folded together with the panels in two along the center line.

What is claimed is:

1. A process for making a disposable diaper formed from a composite web and a liquid-absorbent laminated panel attached to an inner side of said composite web, said process comprising the steps of:

feeding a continuous first web and a continuous second web having a transverse dimension larger than a corresponding dimension of said first web in a machine direction under tension in said machine direction while feeding continuous waist elastic members stretched at a predetermined ratio in said machine direction so as to be laid along transversely opposite side edges of said first web;

placing said first and second webs upon each other so that transversely opposite side edges of said second web extend outwardly of the transversely opposite side edges of said first web, then attaching said elastic members to an inner surface of at least one of said first and second webs and joining said first and second webs to each other to form a composite web;

placing a plurality of said panels each extending in a cross direction on said first web at regular intervals in said machine direction and joining to said first web;

folding zones of said second web extending outwardly of the transversely opposite side edges of said first web inward in a cross direction along the side edges of said first web and joining the folded zones of said second web to said first web and to end zones of said panel in the cross direction;

cutting transversely middle zones of said composite web each extending between each pair of said panels which is adjacent to each other along each of first cutting lines generally describing a circle and folding said composite web inward together with said panels in the cross direction alone the machine direction with said panels lying inside;

joining respective halves of said composite web folded inward together in a vicinity of each of second cutting lines extending in the cross direction on both sides of said first cutting line and cutting said composite web together with said elastic members along said second cutting lines to form a plurality of said diapers arranged in the machine direction;

coating first adhesive zones, each of which continuously extends in the machine direction along each of the transversely opposite side edges of said second web, on an inner surface of said second web with adhesives, while coating second adhesive zones, which extend in the machine direction so as to be spaced one from another by a predetermined dimension in the machine direction and lie between said first adhesive zones and the adjacent side edges of said first web, respectively, on the inner surface of said second web with adhesives; and joining the inner surface of said second web to an outer surface of said first web and the zones of said panel extending in vicinities of its transversely opposite ends by means of the adhesives applied on said first and second adhesive zones.

2. The process according to claim 1, wherein each of said adhesive zones is laid between each pair of said panels which are adjacent to each other in the machine direction.

3. The process according to claim 1, wherein
in the step of coating the second adhesive zones, each pair of adjacent said second adhesive zones are spaced from each other in the machine direction by one adhesive-free zone located corresponding to one of said panel; and
in the step of joining the inner surface of said second web to the outer surface of said first web and said panel by means of said first and second adhesive zones, the folded zones of said second web are not directly bonded by any of said first and second adhesive zones to the first web in any regions that correspond to the adhesive-free zones and overlie the elastic members.

4. The process according to claim 3, wherein,
in the step of coating the second adhesive zones, a width of each said adhesive-free zones as measured in the machine direction is substantially the same as that of the corresponding panel; and
in the step of joining the inner surface of said second web to the outer surface of said first web and said panel by means of said first and second adhesive zones, the adhesives in the first adhesive zones directly bond only the folded zones of said second web to the first web and the end zones of said panels.

5. A process for making a disposable diaper formed from a composite web and a liquid-absorbent laminated panel attached to an inner side of said composite web, said process comprising the steps of:

feeding a continuous first web and a continuous second web having a transverse dimension larger than a corresponding dimension of said first web in a machine direction under tension in said machine direction while feeding continuous waist elastic members stretched at a predetermined ratio in said machine direction so as to be laid along transversely opposite side edges of said first web;

placing said first and second webs upon each other so that transversely opposite side edges of said second web extend outwardly of the transversely opposite side edges of said first web, then attaching said elastic members to an inner surface of at least one of said first and second webs and joining said first and second webs to each other to form a composite web;

placing a plurality of said panels each extending in a cross direction on said first web at regular intervals in said machine direction and joining to said first web;

folding zones of said second web extending outwardly of the transversely opposite side edges of said first web inward in a cross direction along the side edges of said first web and joining the folded zones of said second web to said first web and to end zones of said panel in the cross direction;

cutting transversely middle zones of said composite web each extending between each pair of said panels which is adjacent to each other along each of first cutting lines generally describing a circle and folding said composite web inward together with said panels in the cross direction along the machine direction with said panels lying inside;

joining respective halves of said composite web folded inward together in a vicinity of each of second cutting lines extending in the cross direction on both sides of said first cutting line and cutting said composite web together with said elastic members along said second cutting lines to form a plurality of said diapers arranged in the machine direction;

coating first adhesive zones, each of which continuously extends in the machine direction inside each of the transversely opposite side edges of said first web and along each of the transversely opposite ends of said panel, on the outer surface of said first web with adhesives, while coating second adhesive zones, which extend in the machine direction so as to be spaced one from another by a predetermined dimension in said machine direction and extend in the cross direction from said first adhesive zones to the adjacent side edges of said first web, respectively, on the outer surface of said first web;

joining the inner surface of said second web to the outer surface of said first web and the zones of said panel extending in vicinities of its transversely opposite ends by means of the adhesives applied on said first and second adhesive zones.

6. The process according to claim 5, wherein in the step of coating the second adhesive zones, each pair of adjacent said second adhesive zones are spaced from each other in the machine direction by one adhesive-free zone located corresponding to one of said panel; and in the step of joining the inner surface of said second web to the outer surface of said first web and said panel by means of said first and second adhesive zones, the folded zones of said second web are not directly bonded by any of said first and second adhesive zones to the first web in any regions that correspond to the adhesive-free zones and overlie the elastic members.

7. The process according to claim 6, wherein, in the step of coating the second adhesive zones, a width of each said adhesive-free zones as measured in the machine direction is substantially the same as that of the corresponding panel; and in the step of joining the inner surface of said second web to the outer surface of said first web and said panel by means of said first and second adhesive zones, the adhesives in the first adhesive zones directly bond only the folded zones of said second web to the first web and the end zones of said panels.

8. A process of manufacturing disposable diapers, said process comprising the steps of:

feeding a continuous first web in a machine direction;

feeding a continuous second web in the machine direction, wherein a transverse dimension of said second web as measured in a cross direction perpendicular to the machine direction is greater than that of said first web;

placing said first and second webs upon each other so that transversely opposite lateral zones of said second web extend in the cross direction outwardly beyond transversely opposite side edges of said first web, respectively;

feeding continuous waist elastic members stretched at a predetermined ratio in said machine direction between said first and second webs, so that said elastic members extend along and are located between the transversely opposite side edges of said first web;

attaching said elastic members to at least one of facing inner surfaces of said first and second webs, and bonding the inner surfaces of said first and second webs to each other to form a composite web;

placing a plurality of absorbent panels, each of which is elongated in the cross direction, on an outer surface of said first web at regular intervals in said machine direction, and bonding said panels to the outer surface of said first web;

folding the lateral zones of said second web inwardly, in the cross direction, and along the transversely opposite side edges of said first web to cover end zones of said panels;

bonding the folded lateral zones of said second web to at least one of (i) the outer surface of said first web and (ii) the end zones of said panels, except in regions where said folded lateral zones both overlie the elastic members and extend along the adjacent end zones of said panels;

cutting said composite web along first cutting lines located between adjacent said panels to form leg holes of the diapers to be manufactured;

folding said composite web in the cross direction with said panels lying inside;

joining respective halves of said folded composite web in vicinities of second cutting lines, each of which extends in the cross direction and is located between one pair of adjacent said panels; and cutting said folded composite web together with said elastic members along said second cutting lines to obtain individual said diapers.

9. The process according to claim 8, further comprising coating adhesive material on the inner surface of said second web in the lateral zones thereof to form first adhesive zones each extending continuously in the machine direction and along one of transversely opposite side edges of the second web, and second adhesive zones and adhesive-free zones arranged alternatingly in the machine direction, wherein said second adhesive zones and adhesive-free zones are located between said first adhesive zones and the adjacent side edges of said first web, respectively;

wherein the folded lateral zones of said second web are bonded to both (i) the outer surface of said first web and (ii) the end zones of said panels by said first adhesive zones;

the folded lateral zones of said second web are bonded to the outer surface of said first web by said second adhesive zones each of which is located between one pair of adjacent said panels; and the folded lateral zones of said second web are bonded to neither of (i) the outer surface of said first web and (ii) the end zones of said panels in said adhesive-free zones.

10. The process according to claim 8, further comprising coating adhesive material on the outer surface of said first web to form first adhesive zones each extending continuously in the machine direction and along the end zones of said panels, and second adhesive zones and adhesive-free zones arranged alternatingly in the machine direction, wherein said second adhesive zones and adhesive-free zones are located between said first adhesive zones and the adjacent side edges of said first web, respectively;

wherein the folded lateral zones of said second web are bonded to both (i) the outer surface of said first web and (ii) the end zones of said panels by said first adhesive zones;

the folded lateral zones of said second web are bonded to the outer surface of said first web by said second adhesive zones each of which is located between one pair of adjacent said panels; and the folded lateral zones of said second web are bonded to neither of (i) the outer surface of said first web and (ii) the end zones of said panels in said adhesive-free zones.

11. The process according to claim 9, wherein, in the step of coating adhesive material, a width of each said adhesive-free zones as measured in the machine direction is substantially the same as that of the adjacent end zone of the corresponding panel.

12. The process according to claim 10, wherein, in the step of coating adhesive material, a width of each said adhesive-free zones as measured in the machine direction is substantially the same as that of the adjacent end zone of the corresponding panel.

13. The process according to claim 8, wherein both said first and second webs are made from liquid-impervious or hydrophobic materials.

* * * * *